United States Patent [19]
Tobias

[11] Patent Number: 5,457,528
[45] Date of Patent: Oct. 10, 1995

[54] IDENTIFICATION AND QUANTIFICAATION OF REFRIGERANTS

[76] Inventor: Reginald Tobias, 822 Langen Rd., Lancaster, Mass. 01523

[21] Appl. No.: 38,892

[22] Filed: Mar. 29, 1993

[51] Int. Cl.⁶ .............................. G01N 7/00; G01N 9/24
[52] U.S. Cl. .................... 356/300; 250/339.12; 356/319; 73/61.48
[58] Field of Search .................... 356/300, 319, 356/320, 317, 318; 250/339, 343, 339.12, 339.13

[56] References Cited

U.S. PATENT DOCUMENTS

| | | | |
|---|---|---|---|
| 3,696,247 | 10/1972 | McIntosh et al. | 250/339.13 |
| 4,300,689 | 11/1981 | Franklin et al. | 356/407 |
| 4,785,184 | 11/1988 | Bien et al. | 250/339.12 |
| 4,942,134 | 7/1990 | Winefordner et al. | 356/318 |
| 5,001,346 | 3/1991 | Barkhoudarram | 250/339.13 |
| 5,061,075 | 10/1991 | Alfano et al. | 356/318 |
| 5,116,759 | 5/1992 | Klainer et al. | 435/288 |
| 5,257,085 | 10/1993 | Ulich et al. | 356/318 |
| 5,280,177 | 1/1994 | Bruno | 356/246 |

*Primary Examiner*—Robert P. Limanek
*Assistant Examiner*—Alexander Oscar Williams
*Attorney, Agent, or Firm*—George E. Kersey

[57] ABSTRACT

Method and apparatus for identifying a refrigerant by determining the spectrum of the refrigerant in the absence of a sensing reagent and converting the spectrum into an indicium of the type of refrigerant.

21 Claims, 4 Drawing Sheets

IDENTIFICATION AND QUANTIFICAATION OF REFRIGERANTS

FIELD OF THE INVENTION

This invention relates to the refrigerants, and more particularly to their identification by type and composition, and their quantification as to amount and percentage of total constituents.

DESCRIPTION OF RELATED ART

The identification and quantification of refrigerants is important in the reclamation and reuse of refrigerants, as well as in the development of new refrigerants.

A commonly used refrigerant employed by industry has the designation "FREON 22" of the dupont Company, Wilmington, Del. FREON 22 is used extensively, for example, in air conditioning systems. However, FREON 22 is chlorodifluoromethane ($CHClF_2$) and is a chlorinated fluorocarbon ("CFC" or "HCFC") which is thought to attack the atmospheric "ozone layer", making it particularly damaging to the environment. As a result, it is anticipated that the production of FREON 22 and other CFC's will be gradually discontinued. CFC's generally will be replaced by new refrigerants, such as duPont's "SUVA" COLD MP, also known as "134a" which is being developed for use in automotive air conditioning systems and is 1,1,1,2 tetrafluoroethane ($CH_2FCF_3$). This a halogenated or fluorinated hydrocarbon which does not contain chlorine.

Many of the "environmentally friendly" new refrigerants now under development may not be compatible with the existing CFC's seals or lubricants and require new air conditioning components. Existing automotive air conditioning systems may be serviced using ternary blends; i.e. containing three different components. In addition, it is anticipated that in a few years, the entire refrigeration industry will be using several different types of refrigerants. Already, several different refrigerants are being used in commercial refrigeration. Accordingly, it is important to be able to identify the different kinds of refrigerants.

Moreover, if a refrigerant is to be reclaimed, it is necessary to know the type of refrigerant before beginning the reclamation process in order to avoid undesired mixing. Once refrigerants are mixed, they cannot easily be separated. A large tank of reclaimed refrigerant is generally ruined if it contains a mixture of different refrigerants. Instead of being reused, a tank containing a mixture of different refrigerants must be disposed of. The present practice, where the used refrigerant, by law, can not be released into the atmosphere, to employ incineration. But incineration also is objectionable as being wasteful and contributing to air pollution.

Various methods of identifying refrigerants have been employed by the prior art, including gas chromatography, and various techniques for the measurement of physical properties, such as temperature/pressure relationships and temperature/sonic velocity relationships. Of these techniques, gas chromatography is recognized as adequate in providing molecular discrimination, and good quantitative measurements of refrigerant mixtures. This technique, however, does not lend itself to inexpensive, portable, and test equipment usable by comparatively unskilled operators of the kind commonly found in the refrigeration service and reclamation industry. Nor does gas chromatography conveniently provide measurement for contaminants, such as water and oil.

On the other hand, measurement techniques based on physical properties do not have adequate sensitivity. In particular, the economics of the reclamation industry require identification of specific CFC's at concentration levels below 2% when mixed with other closely related CFC and other compounds. Also, physical measurements by and large do not indicate or compensate for the presence of water and oil in refrigerants. Specific compound identification and measurement are needed by the industry in order to properly facilitate the economical reclamation of refrigerants. It is an object of the invention to facilitate the identification of refrigerants. A related object is to facilitate the qualification and quantification of refrigerants, including those in refrigerant mixtures.

Another object of the invention is to improve upon the performance of the various methods of identifying refrigerants which have been employed by the prior art, such as temperature/pressure relationships and temperature/sonic velocity relationships.

Still another object of the invention is to inexpensively approach the capabilities of gas chromatography in providing molecular discrimination, and good quantitative measurements of refrigerant mixtures.

A further object of the invention is to provide analytical equipment with the attributes of being inexpensive, portable, and capable of being used by comparatively unskilled operators of the kind commonly found in the refrigeration service and refrigerant reclamation industry.

A still further object of the invention is to provide for the measurement for contaminants, such as water and oil, commonly found in refrigerant systems.

Yet another object of the invention is to exceed the sensitivity of common measurement techniques, such as those based on physical properties, which do not have adequate sensitivity. A related object is to provide identification of impurities with accuracies which are useful to the trade.

SUMMARY OF THE INVENTION

In accomplishing the foregoing and related objects, the invention provides for identifying specific refrigerants, or refrigerant mixtures with a weight-mixture ratio as low as $99/1$ in an air conditioner or storage vessel. In accordance with one aspect of the invention, water concentrations of 10 to 500 ppm and various oil concentrations can be determined.

The invention further provides for identifying a refrigerant before the refrigerant is reclaimed. If the refrigerant is a blend (such as a ternary blends in the automotive market), the invention can identify whether the blend contains the correct mixture of refrigerants thus making it reusable or whether it contains an incorrect mixture of refrigerants (thus making it unreusable). If the air conditioner contains a mixture of two or more different refrigerants, these will be identified as an unusable mixture of refrigerants.

In accordance with the methods of the present invention, the spectra of the refrigerants, in gas or liquid phase, are measured to identify the types of refrigerants in particular refrigeration systems.

In a method of identifying a refrigerant or mixtures of refrigerants in accordance with the invention, the steps include (a) determining the spectrum of known refrigerants and (b) converting the spectrum into an indicium of the type of refrigerant. The determination of said is by means of optical spectral absorption intensity at one or more specific and selected wave length, and the optical spectral absorption intensity of the refrigerant is converted into an indicium of the type of refrigerant.

The refrigerant can be in a vapor phase and applied to a spectrophotometer which illuminates the refrigerant with optical radiation and measures the absorbtion spectrum of the refrigerant. Alternatively, the vapor of the refrigerant can be condensed in the spectrophotometer by the momentary withdrawal of heat energy therefrom.

In accordance with a further method of the invention selected intensities of the absorption spectrum are determined at different wave lengths and used to provide an indicium of the refrigerant associated with the spectrum. The indicia of different refrigerant components are then processed to provide a qualification and quantization of the components.

The specific refrigerants or refrigerant mixtures can be identified in weight-mixture ratios as low as $^{99}/_{1}$ and contaminant concentrations can be determined in the range of from 10 to 500 ppm for water and in various concentrations for oil.

In apparatus of the invention for identifying a refrigerant, the components include a unit for determining the optical spectral absorption intensity of the refrigerant at one or more specific and selected wave lengths, and a unit for converting the measured optical spectral absorption intensities of the refrigerant into an indicium of the type of the refrigerant. To qualify and quantize a refrigerant mixture, a unit is included for determining optical spectral absorption intensities for the constituents of the mixture and the intensities are converted into indicia of the types of refrigerants and their percentages in the mixture.

The refrigerant can be in a vapor phase and the determining unit be a spectrometer which illuminates the refrigerant with monochromatic radiation in order to obtain an absorption spectrum of the refrigerant. The vapor can be condensed in the spectrometer by the momentary withdrawal of heat energy therefrom.

The apparatus of the invention can further include determining selected intensities of the absorption spectrum at different wave lengths to provide an indicium of the refrigerant associated with the spectrum. The indicia of different refrigerant components are processed to provide a qualification and quantization of the components.

In accordance with a further aspect of the invention there is the further inclusion of a unit for preliminarily separating contaminants from the refrigerant. The contaminants are subjected to spectrographic analysis to identify the contaminants and the extent of their concentration in the refrigerant. The specific refrigerants or refrigerant mixtures can be identified in weight-mixture ratios as low as $^{99}/_{1}$, and contaminant concentrations in the range of from 10 to 500 ppm for water and various concentrations for oil.

In accordance with method of fabricating a system for identifying a refrigerant, the steps include (a) providing for determining the optical spectral absorption intensities of the refrigerant at specific and selected wave lengths and (b) providing for converting the optical spectral absorption intensities of the refrigerant into an indicium of the type of refrigerant.

DESCRIPTION OF THE DRAWINGS

Other aspects of the invention will become apparent after considering several illustrative embodiments taken in conjunction with the drawings, in which.

DETAILED DESCRIPTION

Figure 1:
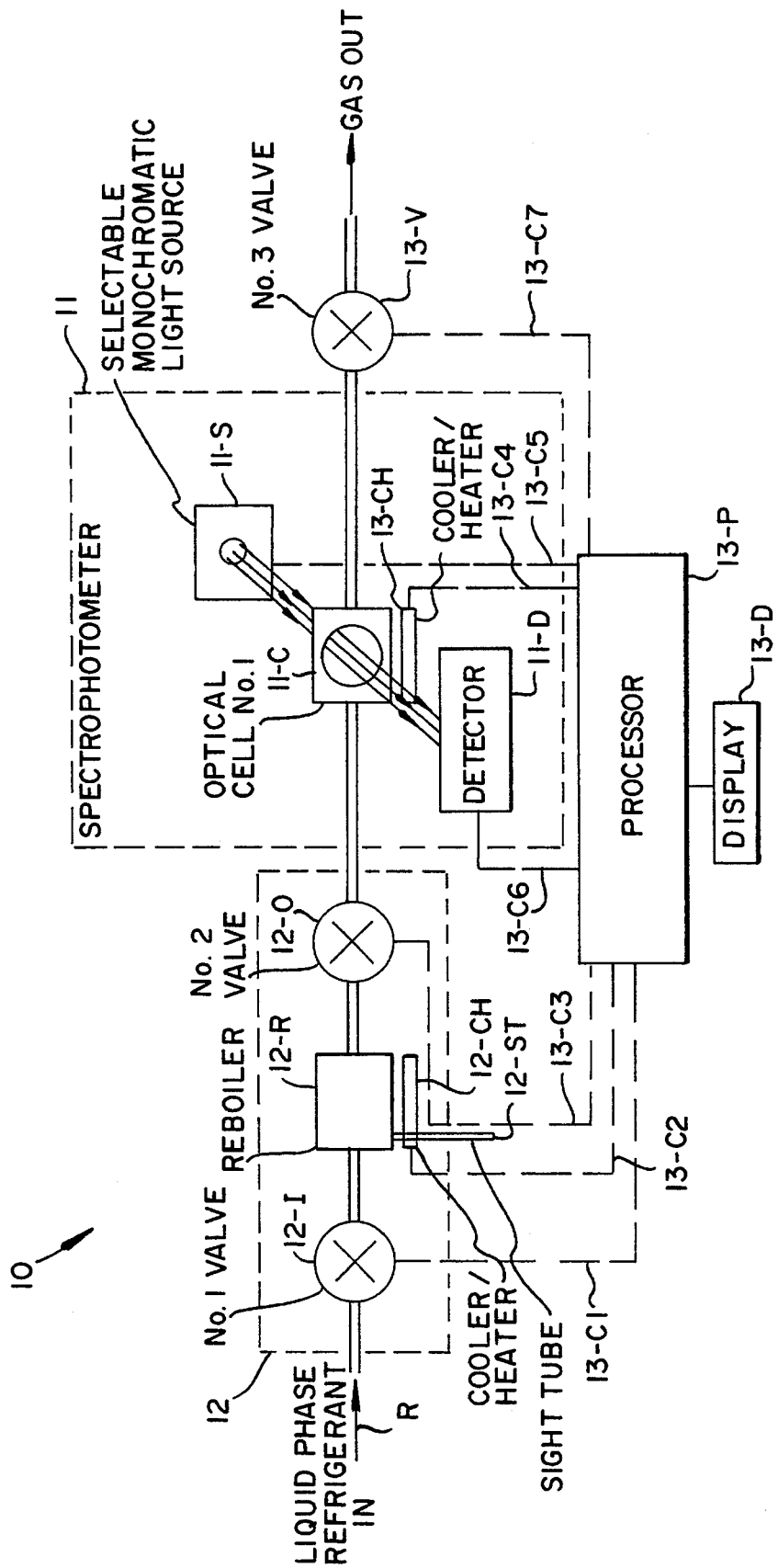
FIG. 1 is a block and schematic diagram of a refrigerant measurement system in accordance with the invention.

With reference to the drawings, the refrigerant measurement system 10 of FIG. 1 includes a spectrophotometer 11 formed by an optical cell 11-c, a selectable light source 11-s, which advantageously is monochromatic, but can be otherwise, and a detector 11-d. The various components 11-c, 11-s and 11-d are standard components employed in the spectrophotometric art. Once a sample to be measured has entered the optical cell 11-c, and treated in accordance with the invention, as described below, the spectral measurement of the sample is by standard spectroscopic techniques.

In order for the sample to be measured by the techniques of the invention, the sample is entered into the cell 11-c through the input stage 12 which includes an input valve 12-i, a reboiler 12-r, including a cooler/heater 12-ch, and an output valve 12-o which applies the sample to the optical cell 11-c.

Control over the measurement process is exercised by a control unit 13 which includes a processor 13-p, a display 13-d, a cooler/heater 13-ch, and output valve 13-v.

In the operation of the system 10, a refrigerant R, which can be either in liquid or gas phase, is applied to the input valve 12-i. The operation of the input valve 12-i is controlled by the processor 13-p over the dashed control line 13-cl. Once the valve 12-i is open, the refrigerant to be tested enters the reboiler 12-r. If the incoming refrigerant is in liquid phase, it is heated by the cooler/heater 12ch in order to initially separate the low vapor pressure fraction refrigerant from the lubricating oils. The cooler/heater 12-ch is operated by the processor 13-p over the control line 13-c2.

The fraction volatilized in the reboiler 12-r, containing oil and water, may be analyzed in a variety of ways. One way is by boiling away the refrigerant and allowing the remaining oil and water to collect in a calibrated glass microbore standpipe 12-st, which can be tapered for better accuracy (range), or may be a straight tube.

The oil and water will separate and be visibly different. The amount of each is calculated from the standpipe calibration.

Another way of analyzing the oil and water is by boiling away the liquid-phase refrigerant and observing the remaining oil and water in a vertical optical cell. There the near infrared absorption spectra may be taken at the 1925 nm (nanometer) spectral band of water, and at the 1725 nm specral band of oil. The intensity of the spectral band is a precise indication of the quantity of the substance.

A further way of analyzing the oil and water is by measuring the infrared absorption spectra of the mixture of refrigerant and contaminant at the 1925 and 1725 bands in an optical cell. The refrigerant is boiled away and recondensed in a second optical cell. The refrigerant is measured at the 1925 and 1725 nm spectral bands, and the readings are subtracted from one another. The remainder is the amount of oil and water in the refrigerant, which can be measured separately if desired.

Continuing with the measurement of refrigerant, the fraction volatilized in the reboiler is then applied through the output valve 12-v, under processor control over dashed line 13-c3, and applied to the optical cell 11-c, where the volatilized fraction is condensed by operation of the cooler/heater 13-ch under processor control exercised over dashed line 13-c4.

Once the condensation is completed, the selectable monochromatic light source 11-s is activated over control line 13-c5 to illuminate the sample in the optical cell 11-c. The light from the source 11-c is monochromatic in that it provides illumination over a restricted range of the electromagnetic spectrum, particularly in the infrared region, and more particularly in the near infrared. It will be appreciated that other bands of light may be selected and that the sample may be illuminated with broadband radiation and the monochromator may be placed in the optical path after the sample.

Figure 2:
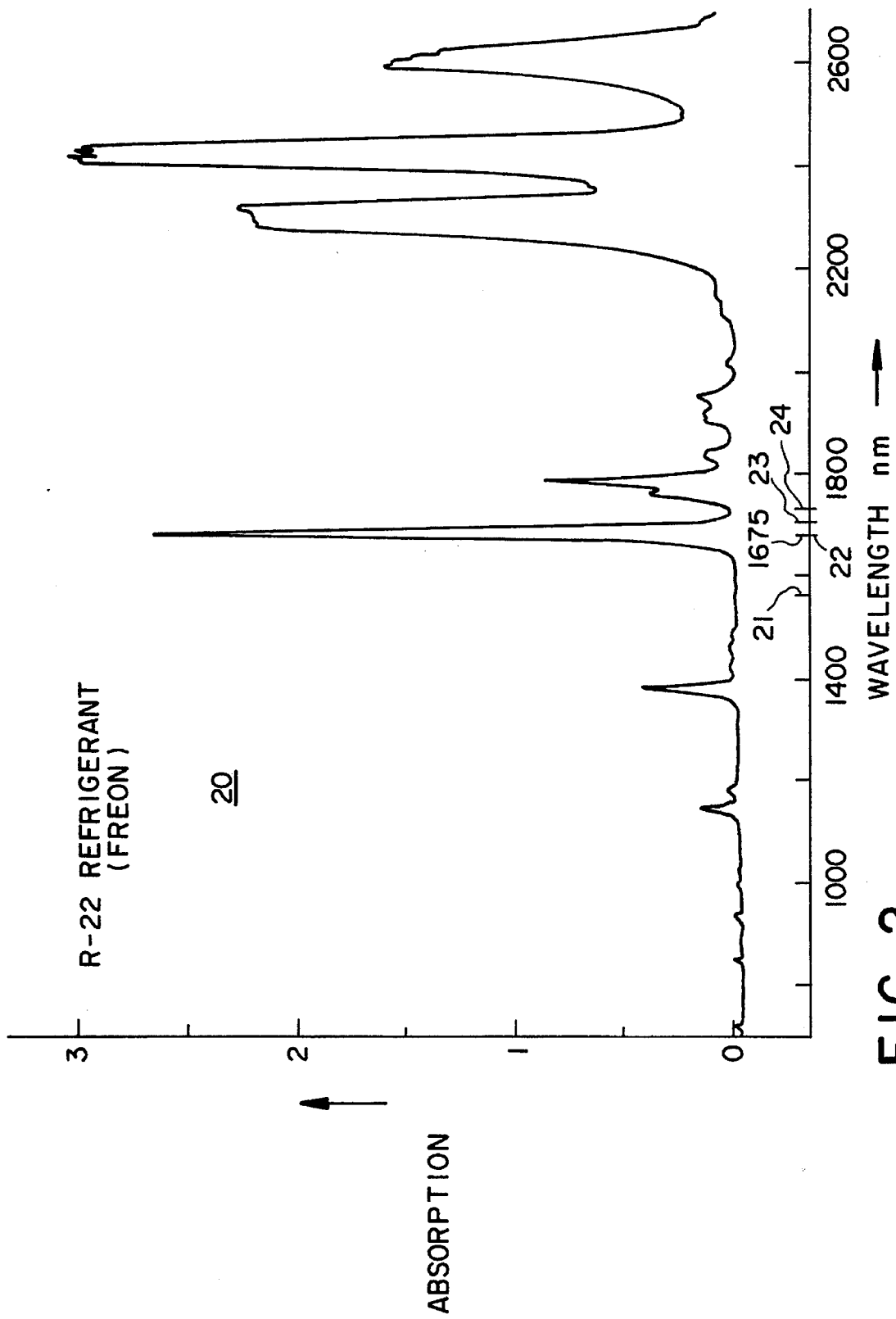
FIG. 2 an illustrative spectrum of FREON 22 obtained using the system of FIG. 1.

The monochromatic light, for example, in the near infrared region, passes through the sample in the optical cell ii-c, which causes absorption of particular frequencies in the illumination depending upon the particular physical characteristics of the sample. An illustrative spectrum for FREON 22 over wavelengths ranging from about 700 to about 2700 nano($10^{-9}$)meters is shown in the graph of FIG. 2. There is virtually no absorption for the lower end of the spectrum between about 1500 and 1650 nanometers, and various absorption peaks, such as the peak at about 1675 nanometers, appear with an increase in wavelength. The way in which the illustrative spectrum is used for the identification of various refrigerant constituents is described below.

The spectrum, such as that of FIG. 2, is monitored by the detector 11-d of FIG. 1 and information concerning the spectrum is applied to the processor 13-p over control line 13-c6, and the spectrum can then be displayed by the unit 13-d.

Once the desired information has been obtained and processed by the unit 13-p, the sample in the optical cell 11-c is evacuated by opening the valve 13-v using dashed control line 13-c7. To assist the evacuation, the cooler/heater 13-ch is energized to assure volatilization of the sample in the optical cell 11-c by the application of heat.

It is to be noted that when the incoming volatile fraction enters the optical cell 11-c, it surprisingly can be condensed to liquid phase by the withdrawal of a relatively negligible amount of heat by operating the cooler/heater 13-ch in its cooling mode.

In using the measurement system 10 for the identification of particular refrigerants, other different refrigerants in pure state are applied to the system 10 for measurement of their particular spectrum and they are coordinated with the test spectrum 20 of FIG. 2, in which, for example, four reference positions 21 thru 24 are selected beginning at a relatively low magnitude of absorption level, and extending through a relatively high magnitude of absorption level.

Figure 3:
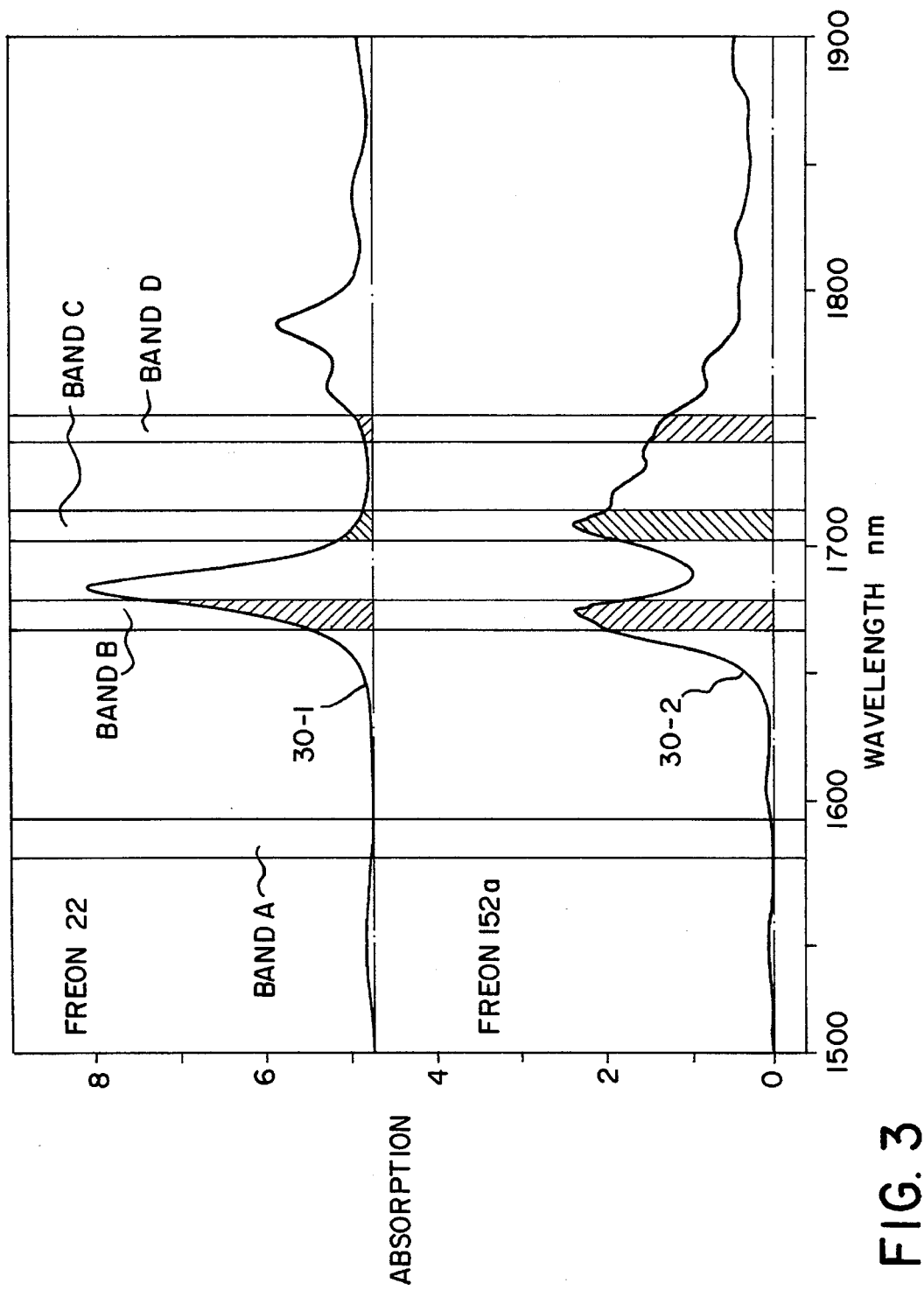
FIG. 3 is a graph with illustrative spectral segments, one of which is a segment of FIG. 2, for use with the system of FIG. 1.

An enlarged segment 30-1 of the spectrum 20 is shown in FIG. 3 with measurements made at Band A, corresponding to reference position 21 of FIG. 2. In addition, measurements are made at Bands B through D, corresponding to positions 22–24 of FIG. 2. It will be appreciated that the measurements are of voltage level, which are inversely proportional to optical densities and are measurable by standard techniques. Since the voltage levels are inversely proportional to absorption, the greatest voltage is measured for Band A. However, the measurements may be made in terms of other parameters. It will be further appreciated that while four bands have been selected, a larger or smaller number of bands may be used. It has been determined that there should be at least two bands, but when the number of bands used is large, a decrease in selectivity may be observed. There is an optimum number of bands, and a matrix of observations can be established. In any case, when the number of bands is greater than four, there is increased system complexity.

An example for producing an analysis is given in equation (1), but there are other ways. The voltages representing the quantized band levels are formed into a reference ratio, as given in equation (1), below:

$$R = \frac{\frac{V_B}{V_A} + \frac{V_C}{V_A} + \frac{V_D}{V_A}}{3} \tag{1}$$

where $V_A$, $V_B$, $V_C$ and $V_D$ are the voltages corresponding to Bands A, B, C and D of FIG. 3;

R is the reference ratio corresponding to the Bands A, B, C and D of FIG. 3.

Also shown in FIG. 3 is an enlarged segment 30-2 corresponding to FREON 152a. Illustrative voltage levels for Bands A though D of segment 30-1 are 10.0, 3.8, 7.8 and 8.1 volts, respectively. For Bands A through D of segment 30-2, the respective voltage levels are 10.0, 3.2, 3.3 and 4.5 volts. For these values, R of 30-1 for FREON 22 is 1.43; while R of 30-2 for FREON 152a is 0.80.

Accordingly, a range of ratios $R_{reference}$ is determined for various refrigerants, and mixtures, that are to be tested. If an unknown refrigerant has a ratio $R_{test}$ that is substantially identical to one of the ratios, it is identified by the corresponding test refrigerant.

However, if $R_{test}$ lies between reference ratios, that indicates that the refrigerant under test is a mixture, and the percentage of the additive is determined by using, for example, a look-up table. Thus for a mixture of FREON 22 and FREON 152a the result of equation (1) is a measurable, significant difference.

Although electrical noise is present when measurements are being made, the method of the invention, nevertheless, can be used to make determinations in most cases with an accuracy of 1%.

Figure 4:
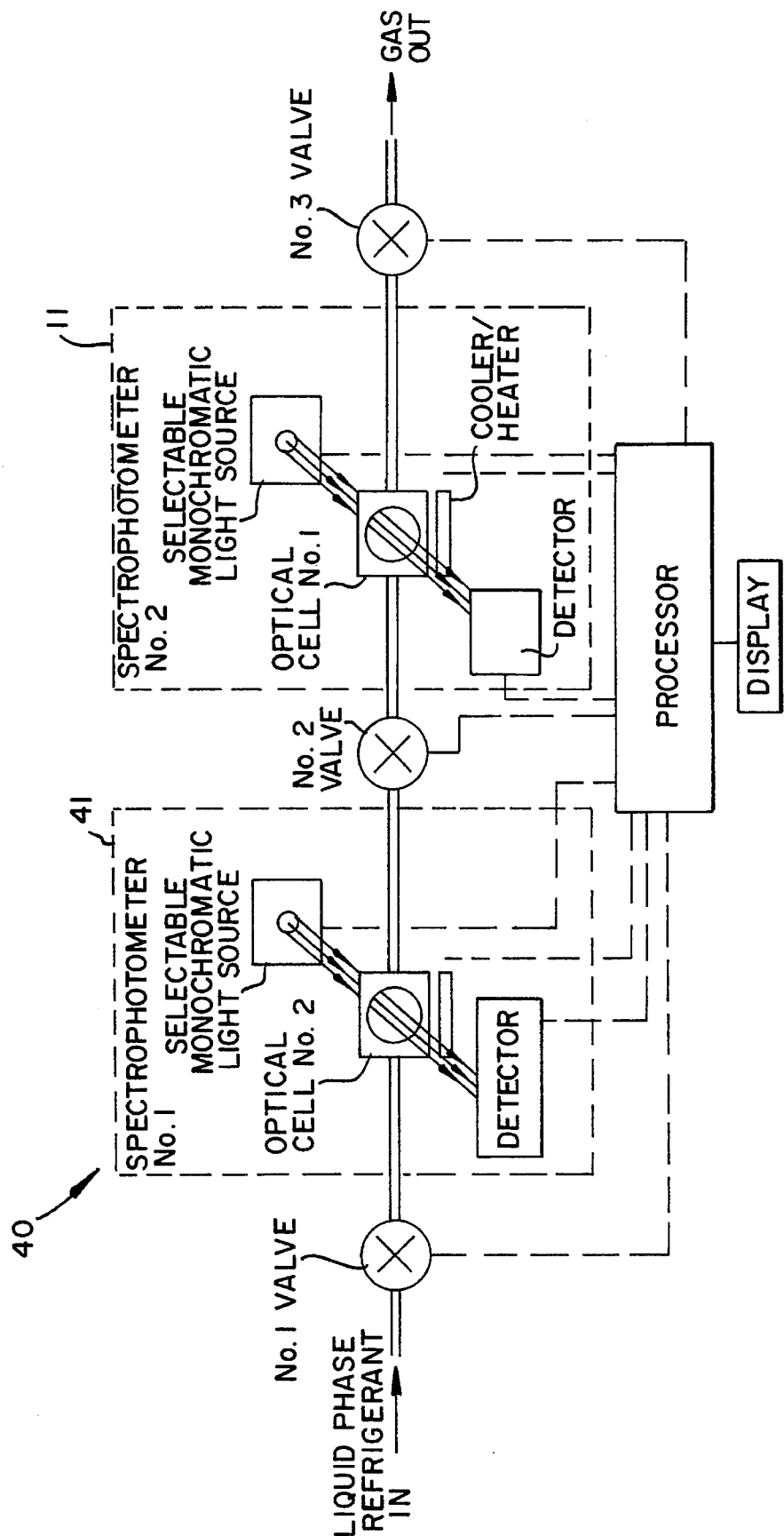
FIG. 4 s a block and schematic diagram of a modified system of the invention for the measurement of contaminants in refrigerants being measured in accordance with the invention.

In addition, to identification of refrigerant constituents, the invention also permits the measurement of contaminants, such as oil and water in a refrigerant system, by using the system 40 of FIG. 4 which is substantially identical to the system 10 of FIG. 1, except for the addition of a second spectrographic arrangement 41 which is the same as the spectrographic arrangement 11.

It will be understood that the foregoing description is illustrative only and that other modifications and adaptations of the invention will be apparent to those of ordinary skill in the art, and that the invention is defined by the claims set forth below.

What is claimed:

1. The method of identifying a refrigerant of unknown type which comprises the steps consisting of:
   (a) determining the spectrum of the refrigerant; and
   (b) converting a multiplicity of readings of said spectrum into an indicium identifying the type of said refrigerant.

2. The method of claim 1 wherein the determination of said spectrum is of optical spectral absorption intensity at a specific and selected wave length, and said optical spectral absorption intensity of said refrigerant is converted into an indicium of the type of said refrigerant.

3. The method of claim 2 for identifying and quantification of a refrigerant mixture wherein optical spectral absorption intensities are determined for the constituents of said mixture and said intensities are converted into indicia of the types of refrigerants and their percentages in said mixture.

4. The method of claim 2 wherein said refrigerant is in a vapor phase and applied to a spectrophotometer which illuminates said refrigerant with optical radiation in order to obtain an absorption spectrum of said refrigerant.

5. The method of claim 4 wherein the vapor of said refrigerant is condensed in said spectrophotometer by the momentary withdrawal of heat energy therefrom.

6. The method of claim 4 wherein selected intensities of said absorption spectrum are determined at different wave lengths and used to provide an indicium of the refrigerant associated with said spectrum.

7. The method of claim 4 wherein indicia of different refrigerant components are processed to provide an identification and quantification of said components.

8. The method of claim 2 wherein contaminants are preliminarily separated from said refrigerants and their volume determined by visual or other means.

9. The method of claim 8 wherein said contaminants are subjected to spectrometric analysis to identify said contaminants.

10. The method of claim 8 wherein specific refrigerants or refrigerant mixtures are identified in weight-mixture ratios as low as $^{99}/_1$ and contaminant concentrations are determined in the range of from 10 to 500 ppm for water and up to 25% for oil.

11. Apparatus for identifying a refrigerant unknown type which comprises:
   (a) means for determining the optical spectral absorption intensity of the refrigerant at a specific and selected wave length; and
   (b) means for converting the measured optical spectral absorption intensity of said unknown type of refrigerant into an indicium of the type of said refrigerant.

12. Apparatus as defined in claim 11 for identifying and quantification of a refrigerant mixture, further including means for determining optical spectral absorption intensities for the constituents of said mixture and said intensities are converted into indicia of the types of refrigerants and their percentages in said mixture.

13. Apparatus as defined in claim 11 wherein said refrigerant is in a vapor phase and the determining means comprises a spectrophotometer which illuminates said refrigerant with optical radiation in order to obtain an absorption spectrum of said refrigerant.

14. Apparatus as defined in claim 13 further including means for condensing the vapor of said refrigerant in said spectrometer by the momentary withdrawal of heat energy therefrom.

15. Apparatus as defined in claim 14 further including means for determining selected intensities of said absorption spectrum at different wave lengths to provide an indicium of the refrigerant associated with said spectrum.

16. Apparatus as defined in claim 14 further including means for processing indicia of different refrigerant components to provide identification and quantification of said components.

17. Apparatus as defined in claim 11 further including means for preliminarily separating contaminants from said refrigerant and measuring the relative volume of said refrigerant.

18. Apparatus as defined in claim 16 further including means for subjecting said contaminants to spectrographic analysis to identify said contaminants and the extent of their concentration in said refrigerant.

19. Apparatus as defined in claim 18 wherein the subjecting means comprises means for identifying refrigerant mixtures in weight-mixture ratios as low as $^{99}/_1$ and identifying contaminant concentrations in the range of from 10 to 500 ppm for water and 0–25% for oil.

20. The method of fabricating a system for identifying a refrigerant of unknown type which comprises:
   (a) providing means for determining the optical spectral absorption intensity of the refrigerant in the absence of a sensing reagent at a specific and selected wave length; and
   (b) providing means for converting the said optical spectral absorption intensity of said refrigerant of unknown type into an indicium of the type of said refrigerant.

21. The method of claim 20 for qualifying and quantizing a refrigerant mixture wherein means are provided for determining optical spectral absorption intensities for the constituents of said mixture and said intensities are converted into indicia of the types of refrigerants and their percentages in said mixture.

* * * * *